United States Patent

Cooper et al.

Patent Number: 5,811,109
Date of Patent: Sep. 22, 1998

[54] HAIR COSMETIC COMPOSITIONS

[75] Inventors: Elizabeth Claire Cooper, Twickenham; Rosemary Jane Welch, Englefield Green, both of Great Britain

[73] Assignee: The Procter & Gamble Company, Cincinnati, Ohio

[21] Appl. No.: 737,651
[22] PCT Filed: Apr. 18, 1995
[86] PCT No.: PCT/US95/04756
 § 371 Date: Nov. 22, 1996
 § 102(e) Date: Nov. 22, 1996
[87] PCT Pub. No.: WO95/32703
 PCT Pub. Date: Dec. 17, 1995

[30] Foreign Application Priority Data

May 28, 1994 [GB] United Kingdom .................. 9410783

[51] Int. Cl.⁶ .................................... A61K 7/48
[52] U.S. Cl. ................. 424/401; 424/70.12; 424/70.15; 424/70.16
[58] Field of Search ................ 424/401, 70.12, 424/70.15, 70.16

[56] References Cited

U.S. PATENT DOCUMENTS

| | | | |
|---|---|---|---|
| 4,192,861 | 3/1980 | Micchelli et al. | 424/47 |
| 4,693,935 | 9/1987 | Mazurek | 428/352 |
| 5,100,658 | 3/1992 | Bolich, Jr. et al. | 424/70 |
| 5,104,646 | 4/1992 | Bolich, Jr. et al. | 424/70 |
| 5,106,609 | 4/1992 | Bolich, Jr. et al. | 424/70 |
| 5,565,193 | 10/1996 | Midha | 424/70.12 |

FOREIGN PATENT DOCUMENTS

93/23446 A  11/1993  WIPO  .............. A61K 7/11

*Primary Examiner*—Thurman K. Page
*Assistant Examiner*—D. Faulkner
*Attorney, Agent, or Firm*—Loretta J. Henderson; Tara M. Rosnell

[57] ABSTRACT

A liquid hair cosmetic composition comprising:
 (A) From about 0.1% by weight to about 10% by weight (acid basis) of a silicone-containing polycarboxylic acid copolymer having a vinyl polymeric backbone, and having grafted to the backbone a silicone-containing macromer having a weight average molecular weight of from about 1,000 to about 50,000. (B) A neutralizing system consisting essentially of sodium hydroxide present at a lever sufficient to neutralize at least about 25% of the acid groups on the silicone containing copolymer; (C) From about 0%–1.0% by weight of water; and (D) The balance comprising a carrier suitable for application to hair. The liquid hair cosmetic products have improved clarity and storage stability and demonstrate excellent hair styling benefits in addition to hair feel attributes and ease of removal and brush out.

17 Claims, No Drawings

HAIR COSMETIC COMPOSITIONS

TECHINCAL FIELD

The present invention relates to hair cosmetic compositions. More particularly, this invention relates to liquid hair cosmetic compositions containing silicone-grafted hair styling polymers having improved long term product stability, hair feel attributes and ease of removal and brush out as well as excellent style retention properties.

BACKGROUND OF THE INVENTION

The desire to have the hair retain a particular shape is widely held. A common methodology for accomplishing this is applying hair styling, or "setting" compositions to the hair, typically to damp or dry hair. These compositions provide temporary setting benefits, and should be removable by water and/or by shampooing. The materials used in the compositions to provide the setting benefits are generally applied in the form of mousses, gels, lotions or sprays.

High levels of style retention, or hold, are typically expected from hair styling compositions applied as a spray. Style retention is typically achieved by the use of resins, such as AMPHOMER, supplied by National Starch, and GANTREZ SP 225, supplied by GAF. As used in commercially sold hairspray products, these resins generally have a weight average molecular weight of from about 40,000 to about 150,000.

When such resins are incorporated into pump and aerosol hairsprays, they can provide suitable style retention attributes. However, such resins are found to be deficient in the area of hair feel and can give a stiff hair feel.

Recently, it has been found that certain neutralisable polymers having silicone macromer portions can provide good style retention benefits to the hair while also providing improved hair feel. In other words, such silicone macromer-containing polymers can impart a tactile sense of softness and conditioning to the hair relative to conventional, non-silicone-containing resins without the tacky hair feel traditionally associated with non-silicone hair fixative polymers. Silicone macromer-containing hair styling polymers and formulations containing them are disclosed, for example, in EP-A-0,408,311 A2 issued Jan. 11th 1991, Hayama, et al., U.S. Pat. No. 5,061,481, issued Oct. 29th 1991, Suzuki et al., U.S. Pat. No. 5,106,609, Bolich et al., issued Apr. 21st 1992, U.S. Pat. No. 5,100,658, Bolich et al., issued Mar. 31st 1992, U.S. Pat. No. 5,100,657, Ansher-Jackson, et al., issued Mar. 31st 1992 and U.S. Pat. No. 5,104,646, Bolich et al., issued Apr. 14th 1992.

It is well known that at least partial neutralisation of the silicone macromer-containing hair styling polymer is necessary to maximise its utility in hair styling compositions. Typically, silicone grafted co-polymers neutralised with potassium hydroxide exhibit good solubility in hairspray compositions containing 15% water. However, potassium hydroxide neutralised systems are less soluble in compositions which contain lower levels of water and lead to hazy, colloidal systems. Moreover, silicone grafted co-polymers which are neutralised with organic neutralisers are found to lead to a somewhat tacky hair feel and are not easily removed from the hair by washing or brush-out.

Thus a need exists for hair styling compositions which have a clear appearance, deliver effective style retention, impart a hair conditioning effect, have a non-sticky hair feel, are easily brushed out and at the same time have stable product and viscosity characteristics and remain fully stable under long term and stressed temperature storage.

SUMMARY OF THE INVENTION

According to one aspect of the invention, there is provided a liquid hair cosmetic composition comprising:
 (a) from about 0.1% by weight to about 10% by weight (acid basis) of a silicone-containing polycarboxylic acid copolymer having a vinyl polymeric backbone, and having grafted to the backbone a silicone-contaning macromer having a weight average molecular weight of from about 1,000 to about 50,000;
 (b) a neutralising system consisting essentially of sodium hydroxide present at a level sufficient to neutralise at least about 25% of the acid groups on the silicone-containing copolymer;
 (c) from 0% to about 1.0% by weight of water; and
 (d) the balance comprising a carrier suitable for application to hair.

The essential, as well as the optional, components of the present invention are described below. All levels and ratios are on a weight basis unless otherwise specified.

The compositions of the present invention contain from about 0.1% to about 10.0%, preferably from about 0.5% to about 8.0% and especially from about 1% to about 6% of specifically defined silicone-containing copolymers. It is these polymers which provide the unique hair conditioning and hair setting characteristics of the present invention. The polymers preferably have a weight average molecular weight of from about 10,000 to about 1,000,000, preferably from about 30,000 to about 300,000, most preferably from about 90,000 to about 300,000 and, preferably, have a Tg of at least about $-20°$ C. As used herein, the abbreviation "Tg" refers to the glass transition temperature of the non-silicone backbone, and the abbreviation "Tm" refers to the crystalline melting point of the non-silicone backbone, if such a transition exists for a given polymer.

The molecular weights and molecular weight distributions of the polymers utilised in the compositions according to the present invention are determined by Size Exclusion Chromatography (SEC). In practise, polymers comprise a distribution of molecular weight species that gives rise to their unique properties. Separation of the molecules is accomplished by Size Exclusion Chromatography (SEC) using a crosslinked polystyrene-divinylbenzene column (MW range $=100-10^7$) with a differential refractive index detector and a differential viscometer. A universal calibrationn curve is prepared from monodispersed polystyrene standards of known molecular weight (MW) and molecular weight distribution (MWD). MW and MWD of the given polymer are determined based on concentration and viscosity responses relative to the calibration.

Preferred polymers comprise a vinyl polymeric backbone, preferably having a Tg above about $-20°$ C. and, grafted to the backbone, a silicone-containing macromer having a weight average molecular weight of from about 1,000 to about 50,000, preferably from about 5,000 to about 40,000, most preferably from about 10,000 to about 20,000. The polymer is such that when it is formulated into the finished hair care composition, when dried, the polymer phase separates into a discontinuous phase which includes the silicone containing macromer and a continuous phase which includes the backbone. It is believed that this phase separation property provides a specific orientation of the polymer on hair which results in the desired hair conditioning and setting benefits.

In its broadest aspect, the copolymers utilized in the present application comprise a silicone-containing monomer (hereafter identified as C) together with a hydrophilic carboxylate-containing monomer (B) and optionally a lipophilic monomer (A).

Examples of useful copolymers and their preparation are described in detail in U.S. Pat. No. 4,693,935, Mazurek, issued Sep. 15th 1987, and U.S. Pat. No. 4,728,571, Clemens et al., issued Mar. 1st 1988. These copolymers comprise monomers A,B and C as defined above. In preferred embodiments, A comprises at least one free radically polymerizable vinyl monomer or monomers and B comprises at least one reinforcing monomer copolymerizable with A and selected from the group consisting of carboxylate-containing monomers and macromers having a Tg or a Tm above about −20° C. B can be up to about 98%, preferably up to about 80%, more preferably up to about 30%, of the total monomers in the copolymer. Monomer C comprises from about 0.1% to about 50.0% of the total monomers in the copolymer.

Representative examples of A (hydrophobic) monomers are the acrylic or methacrylic acid esters of $C_1$–$C_{18}$ alcohols, such as methanol, ethanol, methoxy ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-i-pentanol, 2-methyl-1-pentanol, 3-methyl-1-pentanol, t-butanol (2-methyl-1-propanol), cyclohexanol, neodecanol, 2-ethyl-1-butanol, 3-heptanol, benzyl alcohol, 2-octanol, 6 methyl-1-heptanol, 2-ethyl-1-hexanol, 3.5-dimethyl-1-hexanol, 3,5,5-tri-methyl-1-hexanol, 1-decanol, 1-dodecanol, 1-hexadecanol, 1-octadecanol, and the like, the alcohols having from about 1–18 carbon atoms with the average number of carbon atoms being from about 4–12; styrene; polystyrene macromer; vinyl acetate; vinyl chloride; vinylidene chloride; vinyl propionate; alpha-methylstyrene; t-butylstyrene; butadiene; cyclohexadiene; ethylene; propylene; vinyl toluene; and mixtures thereof. Preferred A monomers include n-butyl methacrylate, isobutyl methacrylate, 2-ethylhexyl methacrylate, methyl methacrylate, t-butylacrylate, t-butylmethacrylate, and mixtures thereof.

Representative examples of B (hydrophilic) neutralisable monomers containing a carboxyl moiety include acrylic acid, methacrylic acid, maleic acid, maleic anhydride, half esters of maleic anhydride, crotonic acid, and itaconic acid. Preferred B monomers include acrylic acid and methacrylic acid and mixtures thereof.

The C monomer preferably has the general formula (I):

$$X\,(Y)_n Si(R)_{3-m} Z_m \qquad (I)$$

wherein X is a vinyl group copolymerizable with the A and B monomers; Y is a divalent linking group; R is hydrogen, $C_1$–$C_4$ alkyl, aryl, alkyl amino, tri($C_1$–$C_4$ alkyl)siloxy or $C_1$–$C_4$ alkoxy; Z is a monovalent siloxane polymeric moiety; n is 0 or 1; and m is an integer from 1 to 3. C has a number average molecular weight of, at least 500, preferably from 1,000 to 50,000. Preferably, the C monomer is selected from one or more monomers having the general formulae (II to VII):

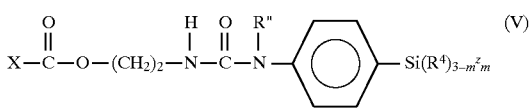

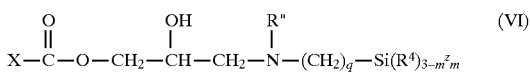

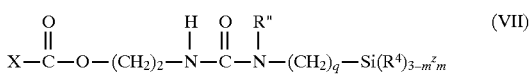

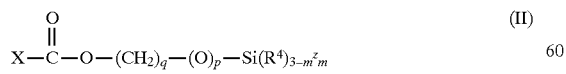

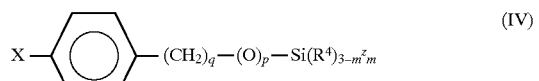

In these structures, m is 1,2 or 3 (preferably m=1); p is 0 or 1; R" is a;lyl or hydrogen; q is an interger from 2 to 6; X is

$R^1$ is hydrogen or —COOH (preferably $R^1$ is hydrogen); $R^2$ is hydrogen, methyl or —$CH_2COOH$ (preferably $R^2$ is methyl); Z is

$R^4$ is alkyl, alkoxy, alkylamino, arly, or hydroxyl (preferably $R^4$ is alkyl); and r is an integer from 5 to 700, preferably from 50 to 500, more preferably from 150 to 300. Of the above, formula II is preferred, particularly when p=0 and q=3.

The polymers utilized herein generally comprise from 0% to about 98% (preferably from about 5% to about 92%, more preferably from about 50% to about 90%) of monomer A, from about 1% to about 98% (preferably from about 7.5% to about 80%) of monomer B, and from about 0.1% to about 50% (preferably from about 0.5% to about 40%, most preferably from about 2% to about 25%) of monomer C. The combination of the A and B monomers preferably comprises from about 50.0% to about 99.9% (more preferably about 60% to about 99.5%, most preferably from about 75% to about 98%) of the polymer.

Preferred silicone-containing copolymers for use herein are selected from:

acrylic acid/n-butylmethacrylate/polydimethylsiloxane (PDMS) macromer—20,000 molecular weight (mw) (10/70/20 w/w/w)

acrylic acid/isobutyl methacrylate/PDMS macromer—20,000 mw (20/60/20 w/w/w)

acrylic acid/PDMS macromer—20,000 mw (80/20 w/w)

t-butylacrylate(tBA)/acrylic acid(AA)/PDMS macromer—10,000 mw (60/20/20)

acrylic acid/isobutyl methacrylate/PDMS macromer—20,000 mw (10/70/20);

acrylic acid/methyl methacrylate/PDMS macromer—20,000 mw (40/40/20);

acrylic acid/isopropyl methacrylate/PDMS macromer—20,000 mw (25/65/15);

acrylic acid/methoxyethyl methacrylate/PDMS macromer 20,000 mw (60/25/15);

acrylic acid/PDMS macromer—20,000 mw (80/20); and mixtures thereof.

The silicone-containing copolymers described above can be synthesized by free radical polymerization of silicone- or polysiloxane-containing monomers with non-silicone- or non-polysiloxane-containing monomers. The general principles of free radical polymerization methods are well understood. See, for example, Odian, "Principles of Polymerization", 2nd edition, John Wiley & Sons, 1981, pp. 179–318.

In compositions according to the invention it can be desirable to purify the silicone containing copolymer by removing unreacted silicone-containing monomer and silicone macromer-grafted polymer with viscosities at 25° C. of about 10,000,000 centistokes and less. This can be done, for example, by hexane extraction. After drying the resin from its reaction solvent, hexane extraction of the reaction product can be performed by adding an excess of hexane to the reaction product and heating to near the Tg of the non-silicone portion of the polymer. The mixture is held at this temperature with stirring for about 30 minutes and cooled to room temperature. The hexane is removed by vacuum suction. Two more hexane extraction cycles are preferably conducted in the same manner as above. After the third cycle, residual hexane remaining with the product is removed by distillation and vacuum drying.

Low molecular weight polysiloxane-containing monomer and polymer is solubilized by supercritical carbon dioxide and transported away from the remaining polymer via a transfer line, which is maintained at identical temperature and pressure as the extraction vessel. The extracted materials are collected in an extraction vessel. Following extraction, the system is depressurised and dry, extracted polymer is recovered from the extraction vessel.

The hair styling polymers herein are utilised in at least partially neutralised form in order to aid shampoo removability of the liquid hair cosmetic compositions. The present development relates to the neutralisation of a hair fixative polymer (eg silicone grafted tBA/AA copolymer) with a neutralisation system consisting essentially of a specific inorganic base, namely sodium hydroxide, in anhydrous or essentially anhydrous aerosol and non-aerosol hairsprays and other hair cosmetic products. In particular the present development relates to improving the clarity, long term storage stability, hair feel attributes and ease of removal characteristics of hairspray and other hair cosmetic products containing no or very low levels of water, approximately 0–1%, preferably 0–0.7% water, by neutralisation of the hair fixative polymer with a neutralisation system comprising at least 80%, preferably at least 95% and more preferably at least 99% by weight of the neutralisation system of sodium hydroxide. While the neutralisation system can be used in excess of the polymer (for example up to 15% excess on an equivalent basis) so as to result effectively in 100% neutralisation of the polymer, nevertheless in preferred compositions, a total of from about 25% to about 95%, preferably from about 40% to about 90%, more preferably from about 55% to about 85%, and especially from about 65% to about 80% of the acidic monomers of the polymer are neutralised.

The amount in grams of inorganic base (Z) required to neutralise a polymer can be deduced from calculations which take into account the acid value of the polymer (A); amount of polymer (W); mol wt of the base (B);,mol wt of the acidic moiety (M) and the degree of neutralisation required (N).

$$Z(g) = W \times A/100 \times 1/M \times B \times N \ \%$$

In the following example the amount of NaOH required to neutralise 2.6 g of acrylic acid co-polymer (with acid value of 20) to a level of 77% neutralisation is calculated.

$$Z(g) = 2.6 \times 20/100 \times 1/72 \times 40 \times 0.77$$

$$Z = 0.222 \ g$$

Note the acid value can be experimentally determined by titrating a specific amount of the polymer with base or theoretically by considering the original acidic content of the co-polymer i.e. a polymer with 20% of acid monomer has an acid value of 20.

As described earlier herein, use of the herein defined neutralising system for at least partial neutralisation of the silicone grafted copolymer leads to anhydrous or essentially anhydrous liquid hair cosmetic compositions of improved clarity and long term storage stability. Product clarity can be measured using a visible range spectrophotometer. Using this equipment the percent transmittance of the sample at 450 nm is measured by calibration against a reference sample of Ethanol B100 as 100% transmittance. Typical transmittance values for opaque systems neutralised with potassium hydroxide neutraliser can be as low as from 1 to 5%. In contrast, the compositions of the invention typically display percent transmittance values greater than 80% when first made, preferred compositions herein displaying 80% transmittance values after storage for at least four weeks at 45 C.

The liquid hair cosmetic compositions of the present invention also include a carrier. This can comprise any of those conventionally used in resin hairspray formulations inclusive of solvents, propellants and other optional ingredients of liquid hair cosmetics. The carrier is generally present in the liquid hair cosmetic compositions at from about 70% to about 99.8%, preferably from about 78% to about 99% by weight. More preferably, the carrier is present at from about 80% to about 98% by weight of the total composition.

Organic solvents suitable for use in the carrier of the present compositions include $C_1$–$C_6$ alkanols and ethers, carbitol, acetone and mixtures thereof. $C_1$–$C_6$ alkanols preferred for use in the present compositions are $C_2$–$C_4$ monohydric alcohols such as ethanol, isopropanol and mixtures thereof. Dimethoxymethane is also a highly preferred solvent.

The performance of the liquid hair cosmetic compositions according to the invention can be improved through the optional incorporation of a nonvolatile plasticizer into the composition. The plasticizer will generally be present in the compositions at up to a level of 25%, preferable from 1% to 20%, more preferably from 1% to 15%. As used herein, "nonvolatile" in regard to plasticizers means that the plasticizer exhibits essentially no vapour pressure at atmospheric pressure and 25° C. The polymer-liquid vehicle solution should not suffer from substantial plasticizer weight loss while the hair cosmetic carrier is evaporating, since this may excessively reduce plasticization of the polymer during use. The plasticizers for use herein should generally have boiling points of about 250° C. or higher.

Plasticizers are well known in the art and are generally described in *Kirk-Othmer Encyclopedia of Chemical Technology*, second edition, Volume 15, pp. 720–789 (John Wiley & Sons, Inc. New York, 1968) under the topic heading "Plasticizers", and by J. Kern Sears and J. R. Darby in the text *The Technology of Plasticizers* (John Wiley & Sons, Inc., New York, 1982). See especially in the Appendix of Sears/Darby Table A. 9 at pages 983–1063 where a wide variety of plasticizers are disclosed.

Plasticizers suitable for use in compositions of the present invention include both cyclic and acyclic nonvolatile materials. Suitable categories of nonvolatile plasticizers include adipates, phthalates, isophthalates, azelates, stearates, citrates, trimellitates, silicone copolyols, iso $C_{14}$–$C_{22}$ alcohols, methyl alkyl silicones, carbonates, sebacates, isobutyrates, oleates, phosphates, myristates, ricinoleates, pelargonates, valerates, camphor, glycols, amine derivatives, selected short chain alcohols and castor oil.

Particularily preferred plasticizers for use herein include glycol and citrate based plasticizers such as propylene glycol, dipropylene glycol, acetyl tri-n-butyl citrate, triethylcitrate, tri-n-butyl and acetyl tri-2-ethoxyhexyl citrate (as supplied by Pfizer under the trade name Citroflex (RTM) and also glycerin, amino methyl propanol (AMP), diisobutyladipate (DIBA) and isopropanol.

The present compositions can be formulated as hairsprays in aerosol or non-aerosol forms. If an aerosol hairspray is desired, a propellant must be included in the composition. This agent is responsible for expelling the other materials from the container and forming the hairspray character.

The propellant gas can be any liquefiable gas conventionally used for aerosol containers. Preferably the density of the propellant or mixture thereof is less than 1 so that pure propellant is not emitted from the container. Examples of materials that are suitable for use as propellants are trichlorofluoromethane, dichlorodifluoromethane, dichlorotetrafluoroethane, monochlorodifluoromethane, trichlorotrifluorethane, dimethylether e.g Dimel 152A (RTM) supplied by Du Pont, propane, n-butane, isobutane, used singly or admixed and propane butane e.g CAP 80 (RTM). Dimel 152A (RTM) and propane butane are preferred.

The amount of the propellant gas is governed by normal factors well known in the aerosol art. For hairsprays the level of propellant is generally from about 10% to about 40%, preferably from about 20% to about 30%, of the total composition. If a propellant such as dimethylether utilizes vapor pressure suppressant (e.g., trichloroethane or dichloromethane) the amount of suppressant is included as part of the propellant.

The hair spray compositions of the present invention can be made using conventional formulation and mixing techniques. Compositions of the present invention can be made by adding the polymer to ethanol and mixing for several hours until dissolved. Plasticizer and neutralising ingredients are then added and the resulting solution is stirred. Any remaining ingredients such as water, ethanol and perfume can then be added.

Methods of making the hair cosmetic compositions of the present invention are described more specifically in the examples.

Alternatively, pressurised aerosol dispensers can be used where the propellant is separated from contact with the hairspray composition by use of specialised containers such as a two compartment can of the type sold under the tradename SEPRO from Americal National Can Corp.

Other suitable aerosol dispensers are those characterized by the propellant being compressed air which can be filled into the dispenser by means of a pump or equivalent device prior to use. Such dispensers are described in U.S. Pat. No. 4,077,441, Mar. 7th 1978, Olofsson and U.S. Pat. No. 4,850,577, Jul. 25th 1989, TerStege. Compressed air aerosol containers suitable for use are also currently marketed by The Procter & Gamble Company under their tradename VIDAL SASSOON AIRSPRAY (RTM) hairsprays.

Conventional non-aerosol pump spray dispensers, i.e., atomizers, can also be used.

The liquid hair cosmetic compositions of the present invention can also contain a variety of non-essential, optional components such as preservatives, surfactants, block polymers, thickeners and viscosity modifiers, electrolytes, fatty alcohols, pH adjusting agents, spreading agents, perfume oils, perfume solubilizing agents, sequestering agents; emollients; lubricants and penetrants such as various lanolin components; protein hydrolysates and other protein derivatives; ethylene adducts and polyoxyethylene cholesterol; sunscreens and volatile and non-volatile silicone fluids. Such conventional optional ingredients are well known in the art, e.g. surfactants such as anionics (e.g., sodium alkyl sulphates, nonionics (amine oxides); amphoterics (aliphatic secondary or tertiary amine derivatives) zwitterionics (aliphatic quaternary ammonium; phosphonium or sulphonium derivatives) and fluorinated surfactants (e.g. Zonyl FSK) (RTM); thickeners and viscosity modifiers such as diethanolamides of long chain fatty acids; block polymers of ethylene oxide and propylene oxide such as Pluronic (RTM) F88 offered by BASF Wyandotte; fatty alcohols such as cetearyl alcohol; viscosity modifiers such as sodium chloride, sodium sulphate, and ethyl alcohol; electrolyte such as earth and alkaline-earth metal salts; quaternary ammonium ions and cationic amines and halogen ions; pH adjusting agents such as citric acid, succinic acid, sodium hydroxide and triethanolamine; spreading agents such as isododecane, perfume oils such as Florasynth (RTM) perfumes; perfume oil solubilizers such as polyethylene glycol fatty acid esters and sequestering agents such as ethylenediamine tetraacetic acid. Each of these optional materials can be present at a level of from about 0.05% to about 5%, preferably from about 0.1% to about 3% by weight of composition.

The liquid hair cosmetic compositions of the present invention are used in conventional ways to provide the hair styling/holding benefits of the present invention. Such method generally involves spraying an effective amount of the product to dry or damp hair before or after the hair is styled, or both. By "effective amount" is meant an amount sufficient to provide the hair volume and style benefits desired considering the length and texture of the hair.

The invention is illustrated by the following non-limiting examples.

In the examples, all concentrations are on a 100% active basis, unless otherwise stated and the abbreviations have the following designation:

| | |
|---|---|
| Hair Styling Polymer | 60% t-butyl acrylate/20% acrylic acid/20% silicone PDMS. Weight average molecular weight (measured by SEC) of 150,000. |
| NaOH | Sodium hydroxide solution, containing 45% sodium hydroxide and 55% water. |
| Solvent | Ethanol |

EXAMPLES I–VI

The following are liquid hair cosmetic compositions in the form of hairspray compositions suitable for pump spray dispensers and which are representative of the present invention:

| | I | II | III | IV | V | VI |
|---|---|---|---|---|---|---|
| Hair Styling Polymer | 3.0 | 2.0 | 4.0 | 6.0 | 2.0 | 5.0 |
| % poly NaOH neutralised | 82 | 70 | 75 | 80 | 85 | 75 |
| Balance | | | to 100 percent with ethanol | | | |

The balance contains ethanol and optional ingredients such as plasticizer (preferably DIBA), perfume and surfactants.

The hairspray formulations are prepared by adding the polymer directly to the ethanol. A magnetic or air driven stirrer is used to mix the ingredients until the polymer is dissolved, typically about 1 to 2 hours. The neutralizing agent is then added and mixed into the premix. Then, the optional ingredients, as may be applicable, are mixed into the composition.

The above compositions provide effective style retention, deliver a hair conditioning effect and have excellent long term clarity and a non-tacky hair feel.

EXAMPLES VII–XII

The following are liquid hair cosmetic compositions in the form of hairspray concentrate compositions suitable for aerosol dispensers and which are representative of the present invention:

|  | VII | VIII | IX | X | XI | XII |
|---|---|---|---|---|---|---|
| Hair Styling Polymer | 4.0 | 2.0 | 5.0 | 6.0 | 3.0 | 7.0 |
| % poly NaOH neutralised | 70 | 78 | 85 | 78 | 80 | 75 |
| Balance | | | to 100 percent with solvent | | | |

As in examples I to VI the balance is ethanol and optional ingredients such as plasticizer (preferably DIBA), perfume and surfactants. The above compositions are prepared as in Examples I–VI. The concentrates are packaged in conventional aerosol spray cans and are charged with a conventional liquifiable propellant such as CAP 80 (RTM) at a propellant: concentrate weight ratio of 23:77.

The above compositions have excellent clarity and stabilizing characterisitcs and when applied to the hair, provide good hair styling and conditioning benefits as well as a non-tacky hair feel and improved ease of removal.

What is claimed is:

1. A liquid hair cosmetic composition comprising:
   a) from about 0.1% by weight to about 10% by weight (acid basis) of a silicone-containing polycarboxylic acid hair styling copolymer having a vinyl polymeric backbone, and having grafted to the backbone a silicone-containg macromer having a weight average molecular weight of from about 1,000 to about 50,000;
   b) a neutralising system consisting essentially of sodium hydroxide present at a level sufficient to neutralise at least about 25% of the acid groups on the silicone-containing copolymer;
   c) from 0% to about 1% by weight of water; and
   d) a carrier suitable for application to hair wherein the carrier comprises an organic solvent for the silicone-containing copolymer consisting essentially of $C_1$–$C_6$ alkanols, $C_1$–$C_6$ ethers, carbitol, acetone, or a mixture thereof.

2. A liquid hair cosmetic composition according to claim 1 wherein the silicone-containing macromer has the general formula (I):

wherein X is a vinyl group; Y is a divalent linking group; R is hydrogen, alkyl, aryl, alkylamino, trialkylsiloxy or alkoxy; Z is a monovalent siloxane polymeric moiety having a number average molecular weight of at least about 500; n is 0 or 1; and m is an integer from 1 to 3.

3. A liquid hair cosmetic composition claim 2 wherein the silicone-containing copolymer has a weight average molecular weight of from 10,000 to 1,000,000 comprising a hydrophilic carboxylate containing monomer (B), optionally a lipophilic, low polarity, free-radically polymerizable vinyl monomer (A) which is copolymerizable with B, and a silicone-containing macromer (C) having a weight average molecular weight of from 1,000 to 50,000, based on polydimethylsiloxane and wherein the macromer (C) is selected from one or more monomers having the general formulae (II–VII):

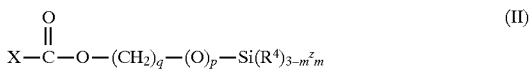

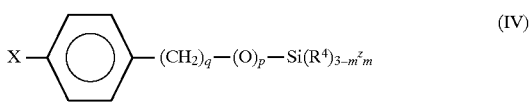

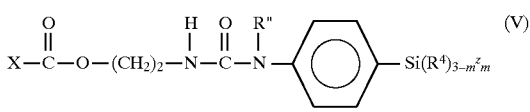

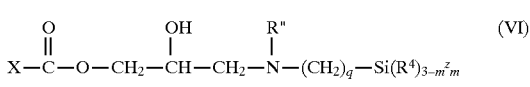

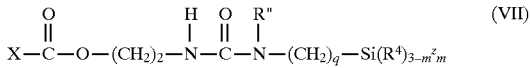

wherein m is 1, 2 or 3; p is 0 or 1; R" is alkyl or hydrogen; q is an integer from 2 to 6; X is

$R^1$ is hydrogen or —COOH; $R^2$ is hydrogen, methyl or —CH$_2$COOH; Z is

$R^4$ is alkyl, alkoxy, alkylamino, aryl or hydroxyl; and r is an integer from 5 to 700; and wherein the silicone-containing copolymer comprises from 0% to 98% monomer A, from 1% to 98% monomer B, and from 0.1% to 50% monomer C.

4. A liquid hair cosmetic composition according to claim 3 wherein the silicone-containing copolymer comprises from 5% to 92% by weight monomer A, from 7.5% to 80% by weight monomer B, and from 0.1% to 50% monomer C.

5. A liquid hair cosmetic composition according to claim 4 wherein monomer A is selected from acrylic acid esters of $C_1$–$C_{18}$ alcohols, methacrylic acid esters of $C_1$–$C_{18}$ alcohols, styrene, polystyrene macromer, vinyl acetate, vinyl chloride, vinyl propionate, vinylidene chloride, alpha-methylstyrene, t-butylstyrene, butadiene, cyclohexadiene, ethylene propylene, vinyl toluene, and mixtures thereof.

6. A liquid hair cosmetic composition according to claim 5 wherein monomer B is selected from acrylic acid, methacrylic acid, maleic acid, maleic anhydride, half esters of maleic anhydride, crotonic acid, itaconic acid and mixtures thereof.

7. A liquid hair cosmetic composition according to claim 6 wherein the silicone containing macromer has the general formula (II) in which p=0 and q=3, m is 1, $R^4$ is alkyl, $R^1$ is hydrogen and $R^2$ is methyl.

8. A liquid hair cosmetic composition according to claim 7 wherein the silicone-containing copolymer is selected from:

acrylic acid/n-butylmethacrylate/polydimethylsiloxane (PDMS) macromer—20,000 molecular weight (mw) (10/70/20);

acrylic acid/isobutyl methacrylate,PDMS macromer—20,000 mw (20/60/20); acrylic acid/PDMS macromer—20,000 mw (80/20 w/w)

t-butylacrylate (tBA)/acrylic acid (AA)/PDMS macromer—10,000 mw (60/20/20) acrylic acid/isobutyl methacrylate/PDMS macromer—20,000 mw (10/70/20);

acrylic acid/methyl methacrylate/PDMS macromer—20,000 mw (40/40/20);

acrylic acid/isopropyl methacrylate/PDMS macromer—20,000 mw (25/65/15);

acrylic acid/methoxyethyl methacrylate/PDMS macromer—20,000 mw (60/25/15);

and mixtures thereof.

9. A liquid hair cosmetic composition according to claim 8 wherein the silicone-containing copolymer is neutralised to a level of from about 40% to about 90% with sodium hydroxide.

10. A liquid hair cosmetic composition according to claim 9 containing less than 0.7% by weight water.

11. A liquid hair cosmetic product comprising a hairspray composition and spray dispenser means for containing and spraying the hairspray composition, and wherein the hairspray composition comprises:

a) from about 0.1% by weight to about 10% by weight (acid basis) of a silicone-containing polycarboxylic acid hair styling copolymer having a vinyl polymeric backbone, and having grafted to the backbone a silicone-contaning macromer having a weight average molecular weight of from about 1,000 to about 50,000;

b) a neutralising system consisting essentially of sodium hydroxide present at a level sufficient to neutralise at least about 25% of the acid groups on the silicone-contaning copolymer;

c) from 0% to about 1% by weight of water; and d) a carrier suitable for application to hair wherein the carrier comprises an organic solvent for the silicone-containing copolymer consisting essentially of $C_1$–$C_6$ alkanols, $C_1$–$C_6$ ethers, carbitol, acetone, or a mixture thereof.

12. A liquid hair cosmetic composition according to claim 3 wherein the silicone-containing macromer (C) has a weight average molecular weight of from about 50,000 to about 40,000.

13. A liquid hair cosmetic composition according to claim 5 wherein monomer A is selected from n-butylmethacrylate, isobutylmethacrylate, 2-ethylhexylmethacrylate, methylmethacrylate, t-butylacrylate, t-butylmethacrylate, and mixtures thereof.

14. A liquid hair cosmetic composition according to claim 6 wherein monomer B is selected from acrylic acid and methacrylic acid and mixtures thereof.

15. A liquid hair cosmetic composition according to claim 9 wherein the level is from about 55% to about 85%.

16. A liquid hair cosmetic composition according to claim 15 wherein the level is from about 65% to about 80%.

17. A liquid hair cosmetic composition comprising:

a) from about 0.1% by weight to about 10% by weight (acid basis) of a silicone-containing polycarboxylic acid hair styling copolymer having a vinyl polymeric backbone, and having grafted to the backbone a silicone-containing macromer having a weight average moleclar weight of from about 1,000 to about 50,000;

b) a neutralising system consisting essentially of sodium hydroxide present at a level sufficient to neutralise at least about 25% of the acid groups on the silicone-containing copolymer; and c) a carrier suitable for application to hair wherein the carrier comprises an organic solvent for the silicone-containig copolymer consisting essentially of $C_1$ –$C_6$ alkanols, $C_1$ –$C_6$ ethers, carbitol, actone, or a mixture thereof;

wherein the composition is essentially free of water.

* * * * *